(12) United States Patent
Raybin et al.

(10) Patent No.: US 11,266,393 B2
(45) Date of Patent: Mar. 8, 2022

(54) TISSUE RETRACTION DEVICE AND DELIVERY SYSTEM

(71) Applicant: BOSTON SCIENTIFIC SCIMED, INC., Maple Grove, MN (US)

(72) Inventors: Samuel Raybin, Marlborough, MA (US); Ryan Wales, Northborough, MA (US); Paul Smith, Smithfield, RI (US); Jeff Gray, Sudbury, MA (US); Sean P. Fleury, Minneapolis, MN (US); Scott E. Brechbiel, Acton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 192 days.

(21) Appl. No.: 16/352,381

(22) Filed: Mar. 13, 2019

(65) Prior Publication Data

US 2019/0282223 A1    Sep. 19, 2019

Related U.S. Application Data

(60) Provisional application No. 62/642,753, filed on Mar. 14, 2018.

(51) Int. Cl.
*A61B 17/02* (2006.01)
*A61B 17/08* (2006.01)
(Continued)

(52) U.S. Cl.
CPC .......... *A61B 17/0218* (2013.01); *A61B 1/018* (2013.01); *A61B 17/08* (2013.01);
(Continued)

(58) Field of Classification Search
CPC ..... A61B 17/0218; A61B 17/22; A61B 17/29; A61B 17/320016
See application file for complete search history.

(56) References Cited

U.S. PATENT DOCUMENTS 4,274,415 A    6/1981    Kanamoto et al.
4,932,955 A    6/1990    Merz et al.
(Continued)

FOREIGN PATENT DOCUMENTS

WO    9600033 A1    4/1996
WO    2009019288 A2    12/2009

OTHER PUBLICATIONS

International Search Report and Written Opinion dated Jul. 3, 2019 for International Application No. PCT/US2019/022073.

*Primary Examiner* — Ellen C Hammond
(74) *Attorney, Agent, or Firm* — Kacvinsky Daisak Bluni PLLC

(57) ABSTRACT

Medical devices and methods of using medical devices are disclosed. An example tissue retraction delivery device includes a positioning assembly, the assembly including: a delivery catheter having a distal end region and a lumen extending therein, wherein the distal end region includes an engagement member orienting tip. The delivery device also includes an actuation catheter extending within at least a portion of the delivery catheter, the actuation catheter including a distal end region and a lumen extending therein. An actuation wire extends within the lumen of the actuation catheter, the actuation wire having a proximal end region and a distal end region. An end effector is coupled to the distal end region of the actuation wire, the end effector configured to capture an engagement member of a tissue retraction device, wherein manipulation of the actuation wire shifts the end effector from a first position to a second closed position.

20 Claims, 20 Drawing Sheets

(51) Int. Cl.
*A61B 17/29* (2006.01)
*A61B 1/018* (2006.01)
*A61B 17/32* (2006.01)
*A61B 17/22* (2006.01)
*A61B 17/00* (2006.01)
*A61B 90/00* (2016.01)
*A61B 17/122* (2006.01)
*A61B 17/128* (2006.01)

(52) U.S. Cl.
CPC .............. *A61B 17/22* (2013.01); *A61B 17/29* (2013.01); *A61B 17/320016* (2013.01); *A61B 17/1227* (2013.01); *A61B 17/1285* (2013.01); *A61B 2017/0034* (2013.01); *A61B 2017/00269* (2013.01); *A61B 2017/00477* (2013.01); *A61B 2017/00876* (2013.01); *A61B 2090/061* (2016.02)

(56) References Cited

U.S. PATENT DOCUMENTS

| | | |
|---|---|---|
| 5,160,339 A | 11/1992 | Chen et al. |
| 5,234,449 A | 8/1993 | Bruker et al. |
| 5,242,456 A | 9/1993 | Nash et al. |
| 5,304,183 A | 4/1994 | Gourlay et al. |
| 5,415,666 A | 5/1995 | Gourlay et al. |
| 5,582,577 A | 12/1996 | Lund et al. |
| 5,899,853 A | 5/1999 | Fowler |
| 5,972,022 A | 10/1999 | Huxel |
| 6,776,783 B1 | 8/2004 | Frantzen et al. |
| 7,112,172 B2 | 9/2006 | Orban, III et al. |
| 7,819,886 B2 | 10/2010 | Whitfield et al. |
| 7,896,891 B2 | 3/2011 | Catanese, III et al. |
| 8,038,612 B2 | 10/2011 | Paz |
| 8,052,700 B2 | 11/2011 | Dunn |
| 8,075,481 B2 | 12/2011 | Park et al. |
| 8,114,098 B2 | 2/2012 | Kimura et al. |
| 8,172,859 B2 | 5/2012 | Matsuno et al. |
| 8,360,972 B2 | 1/2013 | Paz |
| 9,011,325 B2 | 4/2015 | Slaga et al. |
| 9,259,214 B2 | 2/2016 | Galvani |
| 9,289,216 B2 | 3/2016 | Weisshaupt et al. |
| 9,463,003 B2 | 10/2016 | Gordin et al. |
| 2005/0272977 A1 | 8/2005 | Saadat et al. |
| 2007/0250116 A1 | 10/2007 | Raju |
| 2010/0204727 A1 | 8/2010 | Dominguez |
| 2013/0237768 A1 | 9/2013 | Heftman |
| 2014/0235936 A1 | 8/2014 | Baas et al. |
| 2015/0351855 A1 | 12/2015 | Lee et al. |
| 2018/0035997 A1 | 8/2018 | Smith et al. |
| 2019/0099172 A1* | 4/2019 | Wales .................... A61B 1/018 |
| 2019/0336728 A1* | 11/2019 | Unger ................ A61B 17/3205 |

* cited by examiner

TISSUE RETRACTION DEVICE AND DELIVERY SYSTEM

CROSS-REFERENCE TO RELATED APPLICATIONS

This application claims priority under 35 U.S.C. § 119 to U.S. Provisional Application Ser. No. 62/642,753, filed Mar. 14, 2018, the entirety of which is incorporated herein by reference.

TECHNICAL FIELD

The present disclosure pertains to medical devices, and methods for manufacturing medical devices. More particularly, the present disclosure pertains to a tissue retraction device and related delivery system.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example tissue retraction delivery device includes a positioning assembly, the assembly including: a delivery catheter having a distal end region and a lumen extending therein, wherein the distal end region includes an engagement member orienting tip. The delivery device also includes an actuation catheter extending within at least a portion of the delivery catheter, the actuation catheter including a distal end region and a lumen extending therein. The delivery device also includes an actuation wire extending within the lumen of the actuation catheter, the actuation wire having a proximal end region and a distal end region. The delivery device also includes an end effector coupled to the distal end region of the actuation wire, the end effector configured to capture an engagement member of a tissue retraction device, wherein manipulation of the actuation wire shifts the end effector from a first position to a second closed position.

Alternatively or additionally to any of the embodiments above, wherein the end effector includes a first leg having a first jaw and a second leg having a second jaw, and wherein the first jaw is configured to engage with the second jaw when in the closed position.

Alternatively or additionally to any of the embodiments above, wherein the first leg includes a first arcuate portion and the second leg includes a second arcuate portion, and wherein the first arcuate portion is designed to align with the second arcuate portion to define an opening therebetween when the end effector is in the closed position, and wherein the end effector is configured to receive the engagement member within the opening.

Alternatively or additionally to any of the embodiments above, wherein manipulation of the actuation wire to shift the end effector from a first position to a second closed position includes retracting the actuation wire within the lumen of the actuation catheter.

Alternatively or additionally to any of the embodiments above, wherein retracting the actuation wire within the lumen of the actuation catheter draws the engagement member into contact with the distal end region of the actuation catheter.

Alternatively or additionally to any of the embodiments above, wherein contact of the engagement member with the distal end region of the actuation catheter actuates the engagement member from a first configuration to a second open configuration.

Alternatively or additionally to any of the embodiments above, wherein advancing the actuation wire pushes the tissue retraction member out of a distal end of the tubular catheter.

Alternatively or additionally to any of the embodiments above, wherein the orienting tip includes a tapered face.

Alternatively or additionally to any of the embodiments above, wherein retracting the actuation wire within the tubular catheter draws the engagement member into contact with the tapered face of the orienting tip, and wherein rotation of the orienting tip pivots the engagement member within the opening of the end effector.

Alternatively or additionally to any of the embodiments above, wherein a portion of the end effector is magnetic.

Alternatively or additionally to any of the embodiments above, wherein the engagement member includes a projection member extending away from a body portion of the engagement member.

Another example tissue retraction delivery device includes:
a handle;
a delivery catheter having a proximal end coupled to the handle, a distal end region and a lumen extending therein, wherein the distal end region includes an engagement member orienting tip; and
an actuation assembly extending within the lumen of the delivery catheter, the actuation assembly including:
  an actuation catheter having a proximal end region and a distal end region;
  an actuation wire having a proximal end region and a distal end region; and
  a grasper coupled to the distal end region of the actuation wire, the grasper configured to receive an engagement member of a tissue retraction device;
wherein a portion of the actuation assembly is coupled to the handle;
wherein actuation of the handle shifts the grasper from a first position to a second closed position.

Alternatively or additionally to any of the embodiments above, wherein the grasper includes a first leg having a first jaw and a second leg having a second jaw, and wherein the first jaw is configured to mate with the second jaw when in the closed position.

Alternatively or additionally to any of the embodiments above, wherein the first leg includes a first arcuate portion and the second leg includes a second arcuate portion, and wherein the first arcuate portion is designed to align with the second arcuate portion to define an opening therebetween when the grasper is in the closed position, and wherein the grasper is configured to receive the engagement member within the opening.

Alternatively or additionally to any of the embodiments above, wherein actuation of the handle to shift the grasper from a first position to a second closed position includes retracting the actuation wire within the actuation catheter.

Alternatively or additionally to any of the embodiments above, wherein retracting the actuation wire within the actuation catheter draws the engagement member into contact with the distal end region of the actuation catheter.

Alternatively or additionally to any of the embodiments above, wherein contact of the engagement member with the distal end region of the actuation catheter actuates the engagement member from a first configuration to a second open configuration.

Alternatively or additionally to any of the embodiments above, wherein the orienting tip includes a tapered face, and wherein retracting the actuation assembly within the delivery catheter draws the engagement member into contact with the tapered face of the orienting tip.

Alternatively or additionally to any of the embodiments above, wherein rotation of the orienting tip pivots the engagement member within the opening of the grasper.

An example method of dissecting tissue includes:
advancing a tissue retraction device to a target site, the tissue retraction device including:
a positioning assembly, the assembly including:
a delivery catheter having a distal end region and a lumen extending therein, wherein the distal end region includes an engagement member orienting tip, wherein the orienting tip includes a tapered face;
an actuation catheter extending within at least a portion of the delivery catheter, the actuation catheter including a distal end region and a lumen extending therein;
an actuation wire extending within the lumen of the actuation catheter, the actuation wire having a proximal end region and a distal end region; and
an end effector coupled to the distal end region of the actuation wire;
capturing an engagement member of the tissue retraction device within the end effector;
drawing the engagement member into contact with the distal end region of the actuation catheter;
engaging the engagement member with the tapered face of the orienting tip;
rotating the delivery catheter to engage the tapered face with the engagement member such that the engagement member pivots from a first position to a second position; and
attaching the engagement member to the target site.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
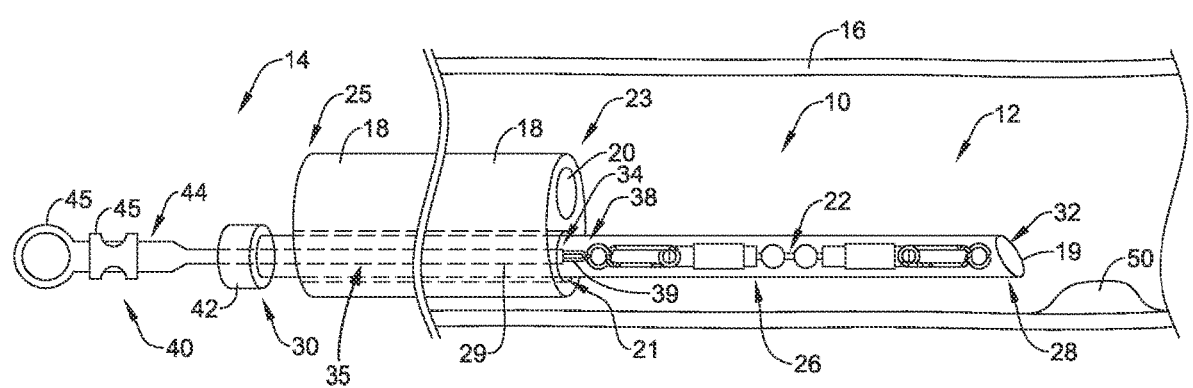
FIG. 1 illustrates a partial cross-sectional side view of an example tissue retraction delivery device positioned within a body lumen.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

A number of medical procedures, including intravascular procedures, procedures along the digestive and/or biliary tract, thoracic procedures, etc. utilize medical devices to access tissue intended for removal (e.g., "target tissue") within the body. For example, in some current medical procedures (e.g., Endoscopic Submucosal Dissection (ESD), Peroral Endoscopic Myotomy (POEM), cholecystectomy, Video-Assisted Thoracoscopic Surgery (VATS)), physicians may utilize an endoscope or similar medical device to access and remove cancerous lesions. Further, as part of the procedure, the physician may utilize an endoscope capable of both accessing the target tissue site while also permitting a cutting device to be deployed therethrough to excise the target tissue. Additionally, in some instances, the endoscope may incorporate features which assist the physician in visualizing and performing the tissue dissection procedure. For example, some endoscopes may include a light and/or camera designed to illuminate the body lumen as the scope is navigated and positioned adjacent to the target tissue site. Additionally, some endoscopes may also include a lumen (e.g., a working channel) through which a cutting member or other accessory medical devices may be deployed and utilized.

While physicians are becoming more proficient at extracting cancerous lesions from within the body (e.g., within the digestive tract, abdominal cavity, thoracic cavity, etc.), the extraction methods continue to be inefficient and time-consuming. For example, in some instances poor visualization of the tissue dissection process may result in a prolonged tissue dissection procedure. In another example, the actual tissue that the physician is attempting to dissect may, itself, obstruct the pathway of the tools which the physician is using during the procedure. Therefore, in some instances it may be desirable to utilize a medical device which assists in improving the visualization of the target tissue while also mitigating the obstruction of dissection tools the physician is utilizing. Therefore, in some instances it may be desirable to utilize a tissue retraction device which lifts and retracts the region of tissue to be dissected by the physician. Disclosed herein are medical devices such as a tissue retraction device and delivery system that are designed to lift and retract the target tissue.

FIG. 1 is a partial cross-sectional side view of an example tissue retraction delivery system 10 including a distal portion 12 and a proximal portion 14. FIG. 1 shows the distal portion 12 of the tissue retraction system 10 positioned within an example body lumen 16. Further, FIG. 1 shows that the proximal portion 14 of the tissue retraction system 10 may extend out of the body lumen 16 to a position outside the body. As shown in FIG. 1, the tissue retraction system may include a tissue retraction device 22.

Additionally, the tissue retraction system 10 may include a delivery catheter 26. The delivery catheter 26 may be constructed from a semi-rigid or compliant material such as a thermoplastic elastomer, silicone rubber, nylon, polyurethane, polyethylene terephthalate (PET), latex, or similar materials. The delivery catheter 26 may have a distal end region and a proximal end region 30. The distal end region of the delivery catheter may include an engagement member orienting tip 28. As shown in FIG. 1, the engagement member orienting tip 28 may include a tapered face portion 19. In other words, the tubular wall defining the distal end region of the delivery catheter 26 may be formed at an angle with respect to the longitudinal axis of the delivery catheter 26. Further, a lumen 32 may extend through the delivery catheter 26 from proximal end region 30 to the distal end region. As illustrated, the tissue retraction device 22 may be positioned along the distal end region and within the lumen 32 of the delivery catheter 26.

Additionally, FIG. 1 illustrates that the delivery catheter 26 (including the tissue retraction device 22) may extend through an example medical device 18. As discussed above, in FIG. 1 the medical device 18 may take the form of an endoscope, laproscope, needle, catheter, guide tube, or the like. The medical device 18 may include a distal portion 23 and a proximal portion 25. Further, FIG. 1 illustrates that the distal portion 23 of the medical device 18 may be advanced within a portion of a body lumen 16 to a position adjacent a target tissue 50, such as a lesion, while the proximal portion 25 of the medical device 18 may extend out of the body lumen 16 to a position outside the body.

Medical device 18 may include a lumen 21 extending from the proximal portion 25 to the distal portion 23 of the medical device 18. In some examples, the lumen 21 may be referred to as the "working channel" of the medical device 18. The lumen 21 may be designed to permit a variety of medical devices to pass therethrough. For example, a physician may pass or exchange a variety of medical devices through the working channel 21 over the course of a given medical procedure. For example, as illustrated in FIG. 1, the delivery catheter 26 (including the tissue retraction device 22) may extend through the lumen 21 of the medical device 18. In other words, FIG. 1 illustrates that a physician may insert the distal end of the delivery catheter 26 into the proximal portion 25 of the medical device 18 (which is outside the body), advance the delivery catheter 26 through the lumen 21 whereby the distal end of the delivery catheter may eventually extend out of the distal portion 23 of the medical device 18 to a position adjacent the target tissue 50.

The proximal end 30 of the delivery catheter 26 may include a control member 42. The control member 42 may be utilized as a grip to control the translation of the delivery catheter 26. Further, the control member 42 may also permit a user to rotate the delivery catheter 26. As will be described in greater detail below, the control member 42 may be utilized by a physician to advance the distal end of the delivery catheter 26 to a position adjacent a target tissue 50 prior to deploying the tissue retraction device 22 from the distal end of the delivery catheter 26.

In some examples, the medical device 18 may include additional features. For example, the medical device 18 shown in FIG. 1 may include an accessory feature 20 (e.g., light, camera, etc.) positioned on the distal portion 23 of the medical device 18. Further, other medical devices 18 having additional features may be utilized in conjunction with the tissue retraction system 10.

As illustrated in FIG. 1, in some examples the tissue retraction system 10 may include a delivery assembly 34. The delivery assembly 34 may include an actuation wire 35 extending within a lumen of an actuation catheter 29. A proximal end of the actuation wire 35 may be coupled to the handle 44. Further, a distal end of the actuation wire 35 may be coupled to the end effector (e.g., a grasper) 39. As will be described in greater detail below, the actuation wire 35 and the end effector 39 may be able to translate with the lumen of the actuation catheter 29.

In some examples, one or more components of the delivery assembly 34 may be designed to advance (e.g., push, deploy, etc.) the tissue retraction device 22 out of the distal end of the delivery catheter 26. For example, advancing the end effector 39 (via the handle 44 and actuation wire 35) in a proximal-to-distal direction within the lumen 32 of the delivery catheter 26 may push the tissue retraction device 22 out of the delivery catheter 26. As will be described in greater detail below, once the end effector 39 has pushed the tissue retraction device 22 out of the delivery catheter 26, it may also be used to position and/or manipulate the tissue retraction device 22 within the body lumen 16.

As discussed above, the delivery assembly 34 may extend within the lumen 32 of the delivery catheter 26. In other words, FIG. 1 illustrates that a distal end 38 of the delivery assembly 34 may extend from the proximal end 30 of the delivery catheter 26 (which is outside the body), through the lumen 32 of the delivery catheter 26 whereby the distal end 38 of the end effector 39 may be positioned adjacent the proximal end of the tissue retraction device 22.

The handle member 44 may include one or more finger grips 45 which permit a user to advance (e.g., translate) one or more components of the delivery assembly 34 within the lumen 32 of the delivery catheter 26. Additionally, as will be discussed in greater detail below, the one or more finger grips 45 may also permit a user to advance (e.g., translate) the actuation wire 35 within the lumen of the actuation catheter 29. In other words, by manipulating the handle 44, a user may be able to translate the actuation wire 35 within the lumen of the actuation catheter 29 while also being able to advance all of the components of the delivery assembly 34 along the longitudinal axis of the delivery catheter 26. The handle design illustrated in FIG. 1 is a schematic. Other handle designs are contemplated. For example, handle designs that include different grip arrangements, ergonomic features, etc. that may be utilized with the tissue retraction system 10 (and components thereof) described herein are contemplated.

The distal end 38 of the delivery assembly 34 may include an end effector 39 (e.g., grasper, forceps, jaws, etc.). When positioned within the lumen 32 of the delivery catheter 26, the end effector 39 may be in a closed position (e.g., the jaws of the grasping member 39 may be closed and contacting one another). Further, as will be discussed in greater detail below, the handle member 44, the actuation catheter 29 and the actuation wire 35 may be utilized (in combination) to control the opening and/or closing of the end effector 39. In other words, when the end effector 39 is advanced to a position outside of the lumen 32 of the delivery catheter 26, a user may manipulate the handle member 44, the actuation catheter 29 and the actuation wire 35 to open and/or close the end effector 39.

As described above, the delivery assembly 34 may be utilized to deploy the tissue retraction device 22 out of the distal end of the delivery catheter 26. Specifically, it can be appreciated that, when positioned adjacent to tissue target 50, a user may advance the delivery assembly 34 in a proximal-to-distal direction within the lumen 32 of the delivery catheter 26 such that the end effector 39 may contact and push the proximal end of the tissue retraction device 22 out of the distal end of the delivery catheter 26.

In at least some examples contemplated herein, the delivery assembly 34 and the tissue retraction device 22 may be positioned within the delivery catheter 26 as depicted in FIG. 1 prior to the delivery catheter 26 being advanced through the lumen 21 of the medical device 18. In other words, in some examples, both the delivery assembly 34 and the tissue retraction device 22 may be "pre-loaded" into the delivery catheter 26 prior to being inserted and advanced through the working channel 21 of the medical device 18 to a position adjacent to target tissue 50. In other examples, however, only the tissue retraction device 22 may be pre-loaded into the delivery catheter 26 and advanced within the lumen 21 of the medical device 18 to a position adjacent to target tissue 50, after which the delivery assembly 34 may be separately inserted into the lumen 21 of the medical device 18 and advanced to a position in which end effector 39 is adjacent and/or contacting the proximal end of the tissue retraction device 22.

It can be appreciated from the above discussion that tissue retraction system 10 may be designed such that the delivery catheter 26 and the delivery assembly 34 may be moved (e.g., translated, rotated, etc.) relative to one another. For example, once the distal end of the delivery catheter 26 is positioned adjacent to the target tissue 50 (with the end effector 39 positioned adjacent to the distal end of the tissue retraction device 22), a user may grasp both the control member 42 and the handle member 44. This may permit the user to maintain the distal end of the delivery catheter 26 in a fixed position while advancing the delivery assembly 34 (including the actuation catheter 29, the actuation wire 35 and the end effector 39) in a distal direction such that the end effector 39 moves distally relative to the distal end of the delivery catheter 26. It can be appreciated that this relative movement may push the tissue retraction device 22 out of the distal end of the delivery catheter 26.

In other examples, it can be appreciated that instead of a user advancing the delivery assembly 34 in a distal direction to deploy the tissue retraction device 22, the user may, alternatively, retract the delivery catheter 26 while maintaining the delivery assembly 34 in a fixed position. The retraction of the delivery catheter 26 may "uncover" the tissue retraction device 22, thereby releasing it from the lumen 32 of the delivery catheter 26.

Figure 2:
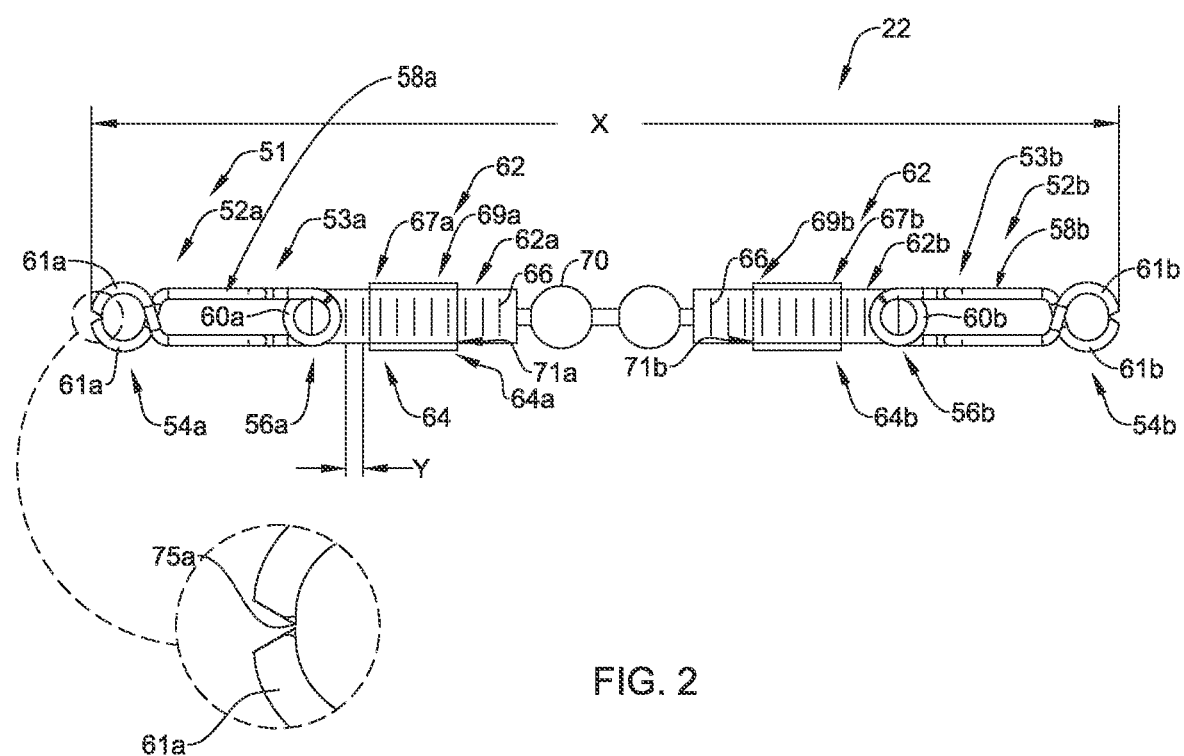
FIG. 2 illustrates a plan view of an example tissue retraction device.

FIG. 2 illustrates an example tissue retraction device 22. The tissue retraction device 22 may include one or more engagement members 51 (e.g., clip, clasp, fastener, clamp, etc.). For example, FIG. 2 illustrates that the tissue retraction device 22 may include a first engagement member 52a and a second engagement member 52b. The first engagement member 52a may include a first end 54a, a second end 56a and a body portion 53a positioned between the first end 54a and the second end 56a. The first end 54a may include a one or more jaws 61a. As will be described further with respect to FIG. 3, the jaws 61a may be designed such that they move relative to one another. FIG. 2 further illustrates that the second end 56a of the first engagement member 52a may include a spring element 60a. It can be appreciated that the spring element 60a may be designed to provide a compressive force that is translated through the body of the first engagement member 52a to the jaw members 61a, thereby biasing the jaw members 61a in a closed position (e.g., a position in which the jaw members 61a are contacting one another). However, the ends of the jaw members 61a may not necessarily contact one another while in a closed position. The jaw members 61a may be spaced apart from one another while in a closed position. Spacing the jaw members 61a apart from one another while in a closed position may permit additional compressive force to be generated when in contact with tissue. This additional compressive force could be termed "preload." The range of preload forces could vary from about 5 grams of force to about 200 grams of force, or about 15 grams of force to about 40 grams of force.

Furthermore, it can be appreciated that the jaw members 61a may be sharpened to exhibit a slope facing the second end 56a of the first engagement member 52a. For example, the detail view of FIG. 2 shows the slope creates a sharp point 75a that may engage tissue more aggressively. The direction of the slope enhances tissue engagement by discouraging captured tissue from disengaging. It can be appreciated that the engagement members 51 depicted in the examples disclosed herein are schematic. In other words, it is contemplated that the engagement members 51 described herein may include alternative design arrangements, features, geometries etc. without departing from the scope of the examples contemplated herein. For example, it is contemplated that the spring 60a of the first engagement member 52a may be positioned in the body 53a of the first engagement member 52a (in other words, the spring 60a may be positioned between the first end 54a and the second end 56a of the first engagement member 52a). Other variations are contemplated.

FIG. 2 further illustrates that the first engagement member 52a may include one or more gripping members 58a. As described above, after the tissue retraction device 22 has been deployed out of the distal end of the delivery catheter 26, the delivery assembly 34 (including the end effector 39, as illustrated in FIG. 1) may be utilized to position and/or attach the tissue retraction device 22 to the target tissue 50 within body lumen 16. It can be appreciated that the gripping members 58a may be designed to engage the end effector 39 (located on the distal end 38 of the actuation wire 35, as illustrated in FIG. 1). In other words, the gripping members 58a may provide an interface for which the end effector 39 may engage, attach, grip, grab, capture, etc. the first engagement member 52a. Furthermore, the gripping members 58a may be designed such that they permit the end effector 39 to efficiently acquire, position (and/or reposition), and open/close the jaws 61a of the first engagement member 52a. While FIG. 2 depicts the gripping members 58a located along the body portion 53a of the first engagement member 52a, it is contemplated that the gripping members 58a may be located along other portions of first engagement member 52a. For example, the gripping members 58a may be positioned on the first end 54a and/or the second end 56a of first engagement member 52a.

As discussed above, the tissue retraction device 22 may include more than one engagement member (e.g., another engagement member in addition to the first engagement member 52a described above). For example, FIG. 2 illustrates that the tissue retraction device 22 may include a second engagement member 52b. The second engagement member 52b may include a first end 54b, a second end 56b and a body portion 53b positioned between the first end 54b and the second end 56b. The first end 54b may include a one or more jaws 61b. As will be described further with respect to FIG. 3, the jaws 61b may be designed such that they move relative to one another. FIG. 2 further illustrates that the second end 56b of the second engagement member 52b may include a spring element 60b. It can be appreciated that the spring element 60b may be designed to provide a compressive force that is translated through the body of the second engagement member 52b to the jaw members 61b, thereby biasing the jaw members 61b in a closed position (e.g., a position in which the jaw members 61b are contacting one another). It can be appreciated that the second engagement member 52b depicted in the examples disclosed herein is schematic. In other words, it is contemplated that the second engagement member 52b described herein may include alternative design arrangements, features, geometries, etc. without departing from the scope of the examples contemplated herein. For example, it is contemplated that the spring 60b of the second engagement member 52b may be positioned in the body 53b of the second engagement member 52b (in other words, the spring 60b may be positioned between the first end 54b and the second end 56b of the second engagement member 52b). Other variations are contemplated.

FIG. 2 further illustrates that the second engagement member 52b may include one or more gripping members 58b. As described above, after the tissue retraction device 22 has been deployed out of the distal end of the delivery catheter 26, the delivery assembly 34 (including the end effector 39, as illustrated in FIG. 1) may be utilized to position and/or attach the tissue retraction device 22 to the target tissue 50 within body lumen 16. It can be appreciated that the gripping members 58b may be designed to engage the end effector 39 (located on the distal end 38 of the actuation wire 35, as illustrated in FIG. 1). In other words, the gripping members 58b may provide an interface for which the end effector 39 may engage, attach, grip, grab, capture, etc. the second engagement member 52b. Further, the gripping members 58b may be designed such that they permit the end effector 39 to efficiently acquire, position (and/or reposition), and open/close the jaws 61b of the second engagement member 52b. While FIG. 2 depicts the gripping members 58b located along the body portion 53b of the second engagement member 52b, it is contemplated that the gripping members 58b may be located along other portions of the second engagement member 52b. For example, the gripping members 58b may be positioned on the first end 54b and/or the second end 56b of the second engagement member 52b.

FIG. 2 further illustrates that the tissue retraction device 22 may include one or more tether members 62 coupled to the first engagement member 52a, the second engagement member 52b or both the first engagement member 52a and the second engagement member 52b. The tether 62 may be referred to as a band, rope, cord, leash, strap, strand, etc. The tether 62 may include a variety of cross-sectional geometries. For example, the tether may be circular, rectangular, triangular, or the like. Further, the tether 62 may be bioabsorbable.

Further, FIG. 2 illustrates a first tether member 62a coupled to the second end 56a of the first engagement member 52a and a second tether member 62b coupled to the second end 56b of the second engagement member 52b. In some examples, the tether members 62a/62b may be rigidly fixed to the second ends 60a/60b of each of the engagement members 52a/52b, respectively. Other designs are contemplated. For example, it is contemplated that tissue retraction device 22 may include a single tether 62 coupled to the first engagement member 52a and the second engagement member 52b.

FIG. 2 further illustrates that in some examples, the tissue retraction device 22 may include a swivel 70. As shown in FIG. 2, the swivel 70 may be positioned between and coupled to the first tether 62a and the second tether 62b. It can be appreciated that the swivel 70 may be designed to permit the first engagement member 52a and first tether 62a to rotate relative to the second engagement member 52b and the second tether 62b. In other words, swivel 70 may permit the first engagement member 52a and first tether 62a to rotate independently around a central axis of the tissue retraction device 22 relative to the second engagement member 52b and the second tether 62b. The swivel 70 may be designed to provide complete rotation (e.g., 360 degree rotation) of the first engagement member 52a and first tether 62a relative to the second engagement member 52b and the second tether 62b. However, in other examples, swivel 70 may be designed provide only partial rotation (e.g., less than 360 degree rotation) of the first engagement member 52a and first tether 62a relative to the second engagement member 52b and the second tether 62b. It can be appreciated that the swivel 70 depicted in the examples disclosed herein is schematic. In other words, it is contemplated that the swivel 70 described herein may include alternative design arrangements, features, geometries etc. without departing from the scope of the examples contemplated herein. For example, it is contemplated that the swivel 70 may be incorporated into one or more of the tether members 62a/62b and/or the engagement members 52a/52b. As will be described below, it is contemplated that the tissue retraction system may include multiple swivels 70.

In at least some examples, the tether members 61a/61b may be elastomeric. In some examples, the tether members 62a/62b may be constructed from an elastomeric material such as latex, Nitrile® rubber, ethylene propylene diene rubber, silicone rubber, chloroprene, polychloroprene (e.g., Neoprene®), polyolefin, thermoplastic elastomer, polyisoprene, etc.

Figure 3:
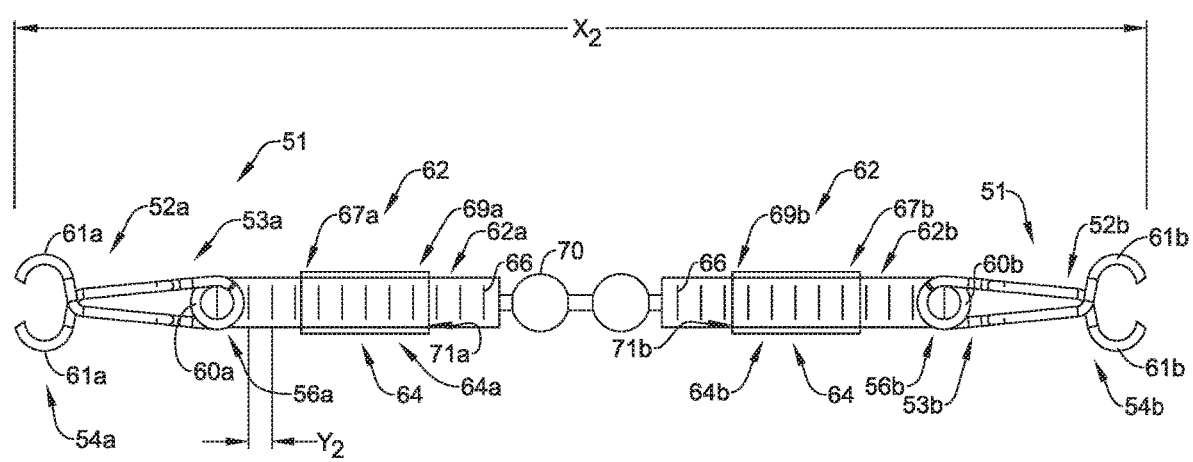
FIG. 3 illustrates a plan view of another example tissue retraction device.

The tether members 62a/62b may elongate from a first, unelongated (e.g., relaxed) position to a second, elongated position. FIG. 2 and FIG. 3 depict the ability of the tissue retraction device 22 to elongate from a first, unelongated position to a second, elongated position. For example, FIG. 2 illustrates the tissue retraction device 22 has an overall length depicted as "X" in FIG. 2 when the tether members 62a/62b are in a relaxed, unelongated configuration. However, when one or more of the tether members 62 is elongated, the overall length of the tissue retraction device 22 elongates to an overall length depicted as "$X_2$" in FIG. 3.

It can be appreciated that when the tissue retraction device 22 is in an elongated position (as shown in FIG. 3), the tissue elongation device is in tension, and therefore includes a retraction force which is pulling the first engagement member 52a toward the second engagement member 52b along the longitudinal axis of the tissue retraction device 22. Furthermore, in some instances it may be desirable for a clinician to know the extent to which the tissue retraction device 22 has elongated (which may be proportional and indicative of the amount of tension that the tissue retraction device 22 is imparting to tissue and/or other body structures to which the engagement members 52a/52b are attached). Therefore, in some examples, the tether members 62a/62b may include a series of reference markers 66 designed to provide visual indicia of the amount of elongation of the first tether member 62a and/or the second tether member 62b.

For example, FIG. 2 illustrates the reference markers 66 spaced substantially equidistant from another along tether member 62a. The distance between adjacent reference markers 66 is depicted as "Y". It is contemplated that the same set of reference markers may be spaced the same distance along tether member 62b. Additionally, FIG. 3 illustrates that as tissue retraction device 22 elongates, the space between the reference markers 66 may lengthen, thereby indicating that the tether member on which they are located has elongated. For example, FIG. 3 shows the space between the reference markers as "$Y_2$" (wherein $Y_2$ is a greater value than Y). It can be appreciated that the reference markers 66 may provide a visual indication of the degree of both the elongation and/or retraction of the tissue retraction device 22. Further, the reference markers 66 may include a variety of markings, symbols, geometric patterns, colors, etc. For example, the markers 66 may include a series of alternating light and dark stripes equally spaced along the tether members 62a/62b. It is further contemplated that a clinician may be supplied with a chart that correlates that degree of separation of the reference markers to the degree of retraction force being generated by the tissue retraction device 22.

As described above, prior to being deployed from the delivery catheter 26, the tissue retraction device 22 may be positioned in an unelongated, relaxed state within the distal end of the delivery catheter. Furthermore, proper alignment of the tissue retraction device 22 within the delivery catheter 26 (prior to deployment) must be maintained to ensure that the tissue retraction device 22 is efficiently deployed within the body lumen 16. For example, it is important to prevent the tissue retraction device 22 from folding and/or wrapping upon itself (e.g., folding back on itself) while being advanced and/or manipulated within the distal end of the delivery catheter 26.

FIG. 2 illustrates that in some examples, the tissue retraction device 22 may include one or more alignment members 64. In some instances, alignment member 64 may be referred to as a sabot, fairing, scaffolding, separator, housing, cover, shell, splitting tube, or the like. For example, the tissue retraction device 22 may include a first alignment member 64a and second alignment member 64b. However, in other embodiments tissue retraction device may include single retraction member. As shown in FIG. 2, first alignment member 64a may be a tubular member having a first end 67a, a second end 69a and a lumen 71a extending therein. Lumen 71a may extend from the first end 67a to the second end 69a. While FIG. 2 depicts the alignment member 64a as a tubular member, other cross-sectional shapes of alignment member 64a are contemplated. For example, the cross-sectional shape of the alignment member 64a may be rectangular, triangular, ovular, square, or the like.

As illustrated, FIG. 2 shows that the alignment member 64a may be disposed along the tether member 62a. For example, in some examples the tether member 62a may extend through the lumen 71a of the alignment member 64a. In at least some examples, the alignment member 64a may permit the tether member 62a to compress into the lumen of the alignment member 64a. Therefore, diameter of the lumen of the alignment member 64a needs to be wide enough to permit the tether member 62a to curl upon itself to be "stored" within the lumen of the alignment member 64a. Allowing the tether member 62a to be stored within the lumen of the alignment member 64a may prevent the tether member 62a from being entangled with the first engagement member 52a.

The alignment member 64a illustrated in FIG. 2 is not intended to be limiting. Rather, in some examples, the alignment member 64a may include two mating plastic components that encapsulate one or both of tether members 62a/62b, one or both the engagement members 52a/52b or both the one or more tether members 62a/62b and the one or more engagement members 52a/52b when the tissue retraction device 22 is in the delivery catheter 26 (prior to deployment).

As discussed above, the tissue retraction device 22 may include more than one alignment member (e.g., another alignment member in addition to alignment member 64a described above). For example, the tissue retraction device 22 may include a second alignment member 64b. As shown in FIG. 2, second alignment member 64b may be a tubular member having a first end 67b, a second end 69b and a lumen 71b extending therein. Lumen 71b may extend from the first end 67b to the second end 69b. While FIG. 2 depicts the alignment member 64b as a tubular member, other cross-sectional shapes of alignment member 64b are contemplated. For example, the cross-sectional shape of the alignment member 64b may be rectangular, triangular, ovular, square, or the like.

As illustrated, FIG. 2 shows that the alignment member 64b may be disposed along the tether member 62b. For example, in some examples the tether member 62b may extend through the lumen 71b of the alignment member 64b. In at least some examples, the alignment member 64b may permit the tether member 62b to compress into the lumen of the alignment member 64b. Therefore, diameter of the lumen of the alignment member 64b needs to be wide enough to permit the tether member 62b to curl upon itself to be "stored" within the lumen of the alignment member 64b. Allowing the tether member 62b to be stored within the lumen of the alignment member 64b may prevent the tether member 62b from being entangled with the second engagement member 52b.

As discussed above, the gripping members described herein may be utilized by the delivery assembly 34 (including the actuation wire 35 and the end effector 39) to open and/or close the jaws 61a/61b of the tissue retraction device 22 described herein. For example, FIG. 3 shows the jaws 61a/61b of the tissue retraction device 22 opened to an expanded configuration.

Figure 4:
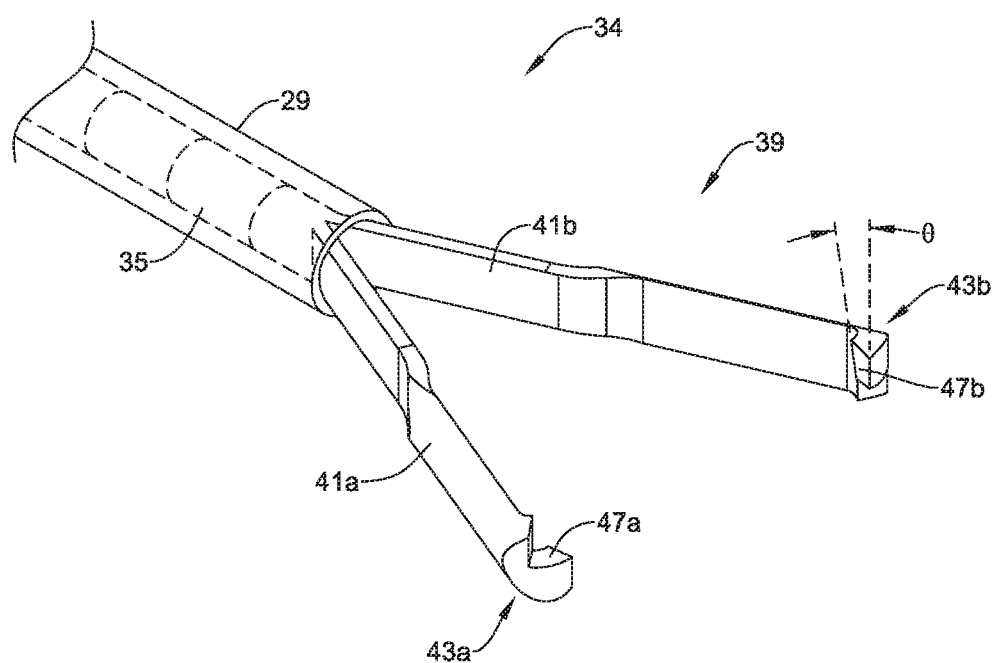
FIG. 4 illustrates a component of an example tissue retraction delivery device.

FIG. 4 illustrates the distal end region of the delivery assembly 34 described above. Specifically, FIG. 4 illustrates the actuation wire 35 extending within the lumen of the actuation catheter 29. Further, FIG. 4 shows the end effector 39 coupled to the distal end of the actuation wire 35.

As illustrated in FIG. 4, the end effector 39 may include a first leg 41a and a second leg 41b. The proximal end of each of the first leg 41a and the second leg 41b may be coupled (e.g., attached) to the distal end of the actuation wire 35. Additionally, FIG. 4 illustrates that each of the first leg 41a and the second leg 41b may be generally elongated members which extend away from the distal end of the actuation wire 35.

FIG. 4 further illustrates that each of the first leg 41a and the second leg 41b may include a first jaw 43a positioned at a distal end region of the first leg 41a and a second jaw 43b positioned at a distal end region of the second leg 41b. FIG. 4 further illustrates that the first jaw 43a may include a first projection 47a and that the second jaw 43b may include a second projection 47b. Each of the first projection 47a and the second projection 47b may curved such that the first projection 47a may face and/or extend in the general direction of the second projection 47b. Additionally, it can be appreciated from FIG. 4 that the first jaw 43a may be designed to mate (e.g., interlock) with the second jaw 43b. In other words, in some examples the first projection 47a of the first jaw 43a may be designed to engage (e.g., interlock) with the second projection 47b of the second jaw 43b.

FIG. 4 further illustrates that each of the first projection 47a and/or the second projection 47b may include an angled portion (depicted in FIG. 4 by the angle "θ"). It can be appreciated that including an angled portion on the first projection 47a and/or the second projection 47b may aid the end effector 39 in aligning a clip at a preferred angle prior to attachment of the clip to a target site (e.g., an angle defined by the angle "θ"). For example, as the first leg 41a and the second leg 41b are closed and engaged together (the end effector 39 is utilized to grasp a clip, for example) a portion of the clip (e.g., a body portion) may be aligned with the angled portion of the first projection 47a and/or the second projection 47b such that the clip is aligned at the angle "θ." In some examples, the angle "θ" may be between 0 and 40 degrees, or between 10 and 35 degrees, or between 20 and 30 degrees.

In some examples, a portion of the end effector 39 may be electromagnetic. For example, in some instances it may be desirable to design the first jaw 43a and/or the second jaw 43b to include an electromagnetic material. Further, while not show in the figures, the tissue retraction system 10 may include a control component (not shown in the figures) located the proximal end of the device (e.g., adjacent the handle member), whereby the control component is designed to activate (or deactivate) the electromagnetic portion of the end effector 39.

Figure 5:
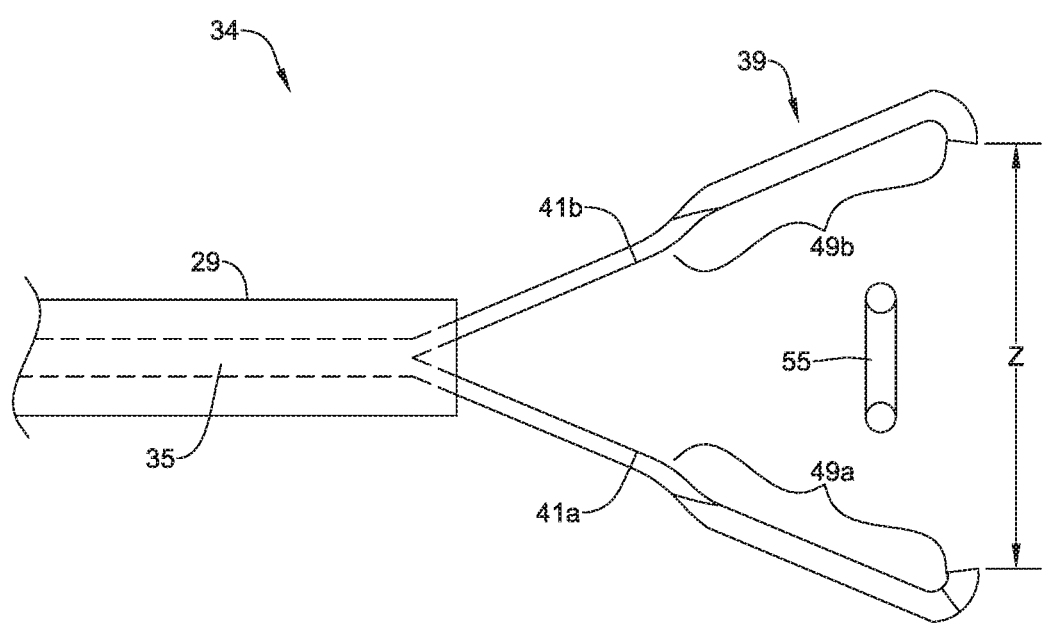
FIGS. 5-7 illustrate a component of an example tissue retraction delivery device shown in FIG. 4 shifting between a first position and a second position.
Figure 6:
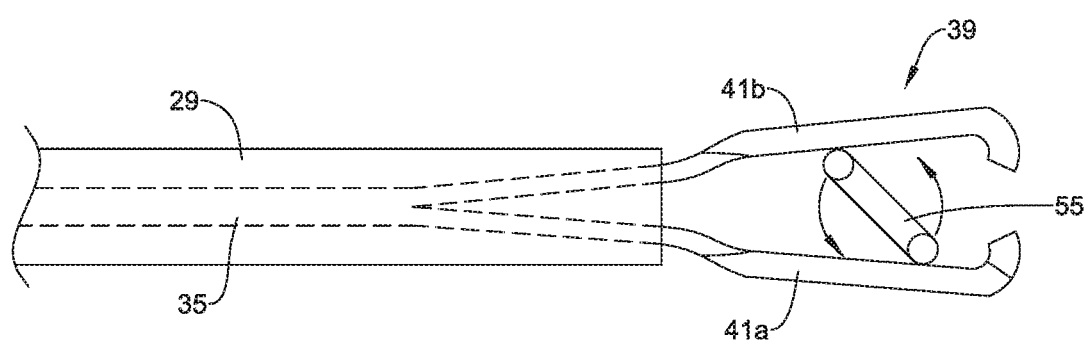
Figure 7:
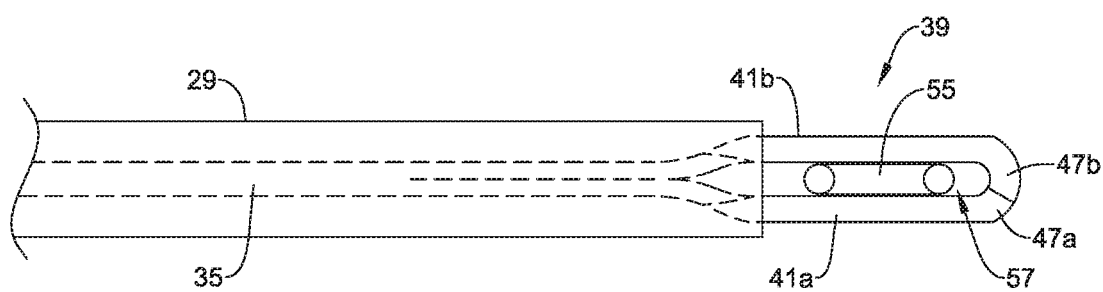

As discussed above, the delivery assembly 34 (including the end effector 39) may be designed to acquire, position (and/or reposition), and open/close the jaws of the engagement members described above. FIGS. 5-7 illustrate a series of steps illustrating the delivery assembly 34 capturing an example engagement member 55 (it can be appreciated that FIG. 5 illustrates an end view of the example engagement member 55). It is noted that the engagement member 55 may be similar in form and function to any of the engagement members described herein. For example, the engagement member 55 may be similar in form and function to the first engagement members 52a/52b described above.

FIG. 5 illustrates the end effector 39 positioned in an open configuration. For example, FIG. 5 shows the distal end of the first leg 41a and the distal end of the second leg 41b of the end effector 39 spaced apart from one another a distance depicted as "Z." It can be appreciated that the distance "Z" may be wide enough to permit the legs 41a/41b of the end effector 39 to extend on either side of the example engagement member 55. In other words, the distance "Z" may be designed to be wide enough to position the engagement member 55 between the first leg 41a and the second leg 41b.

Additionally, FIG. 5 illustrates that the first leg 41a and the second leg 41b of the end effector 39 may include a first arcuate (e.g., curved) portion 49a and a second arcuate (e.g., curved) portion 49b, respectively. As will be described in greater detail below, first curved portion 49a and a second curved portion 49b may be designed to align with one other to form an opening (e.g., aperture).

Further, FIG. 5 illustrates that each of the first leg 41a and the second leg 41b is almost fully extended out of the distal end of the lumen of the actuation catheter 29. It can be appreciated that advancing the first leg 41a and the second leg 41b out of the distal end of the lumen of the actuation catheter 29 may permit each of first leg 41a and the second leg 41b to flex away from one another, thereby allowing the distal ends of the first leg 41a to be spaced away from the distal end of the second leg 41b the distance "Z" as described above.

FIG. 6 illustrates the first leg 41a and the second leg 41b of the end effector 39 shifting toward one another as the end effector 39 is capturing the engagement member 55 between the first leg 41a and the second leg 41b. It can be appreciated from FIG. 6 that retracting the actuation wire 35 within the lumen of the actuation catheter in a distal-to-proximal direction may squeeze the first leg 41a and the second leg 41b together as they enter the distal end of the actuation catheter 29. It can be appreciated that squeezing the proximal end regions of both the first leg 41a and the second leg 41b together may shift the distal end region of the first leg 41a toward the end region of the second leg 41b, as described above.

FIG. 6 further illustrates each of the first leg 41a and the second leg 41b contacting a portion of the example engagement member 55. It can be appreciated that as each of the first leg 41a and the second leg 41b contact the example engagement member 55, the engagement member may rotate (as shown by the arrows 82). As will be discussed in greater detail below, it may be beneficial to design the first leg 41a and the second leg 41b such that they cause the engagement member 55 to rotate and self-align along the first leg 41a and the second leg 41b.

FIG. 7 illustrates the end effector 39 in a closed configuration. Compared to FIG. 6, FIG. 7 shows the actuation wire 35 having been further retracted within the lumen of the actuation catheter 29 in a distal-to-proximal direction. It can be appreciated that the continued retraction of the actuation wire 35 within the lumen of the actuation catheter 29 may further squeeze the first leg 41a and the second leg 41b together. Additionally, in some examples, as the first leg 41a and the second leg 41b are squeezed together, the first projection 47a of the first leg 41a may interlock with the second projection 47b of the second leg 41b.

As described above, FIG. 7 further illustrates that when in the closed configuration, the first leg 41a and the second leg 41b align to form an opening 57 within which the engagement member 55 is captured (e.g., received, positioned, etc.). It can be appreciated that the end effector 39 may be designed such that the compressive force exerted by the first leg 41a and the second leg 41b upon the engagement member 55 may be sufficient to prevent the engagement member 55 from slipping entirely out of the opening 57, while also permitting the engagement member 55 to slide along the opening as the actuation wire 35 is further retracted within the actuation catheter 29.

Figure 8:
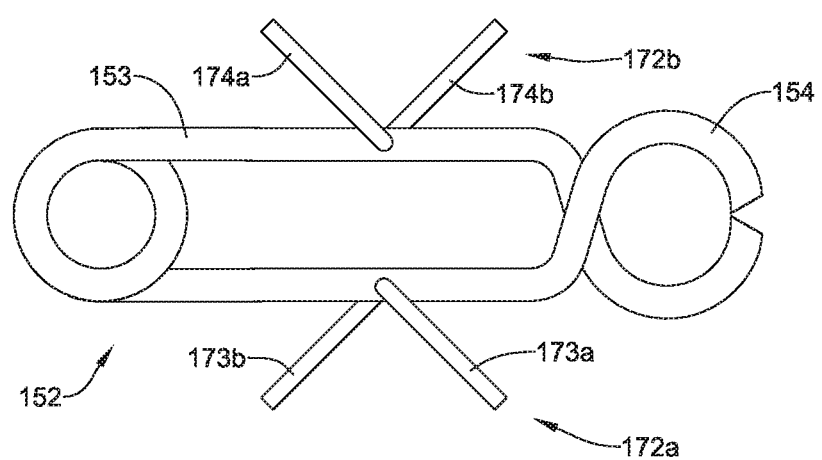
FIG. 8 illustrates a component of an example tissue retraction device.

FIG. 8 illustrates an example engagement member 152. The engagement member 152 may be similar in form and function to other engagement members disclosed herein. For example, the engagement member 152 may be similar in form and function to the engagement members 52a/52b described above. For example, the engagement member may include a body portion 153 and a first end 154. The first end 154 may be configured to attach to a target site in the body.

FIG. 8 further illustrates that the engagement member 152 may include a first projection 173a and/or a second projection 173b. It can be appreciated that, collectively, the first projection 173a and the second projection 173b may define a first "pair" of projections 172a. The first projection 173a and/or the second projection 173b may be elongated members which extend away from the body portion 153 of the engagement member 152. As will be discussed in greater detail below, it can be appreciated that the first projection 173a, the second projection 173b or both the first projection 173a and the second projection 173b may be designed to space the body portion 153 of the engagement member 152 away from a vessel wall.

Additionally, in some examples, the first pair of projections 172a (including the first projection 173a and/or the second projection 173b) may be "spring loaded." For example, the first projection 173a and/or the second projection 173b may be able to bend and/or flex such that it aligns with the body portion 153 of the engagement member 152 while the engagement member 152 is positioned within a delivery system. Further, the first projection 173a and/or the second projection 173b may shift to the configuration shown in FIG. 8 after the engagement member 152 is deployed out of the delivery system.

FIG. 8 further illustrates that the engagement member 152 may include a third projection 174a and/or a fourth projection 174b. It can be appreciated that, collectively, the third projection 174a and the fourth projection 174b may define a second "pair" of projections 172b. As illustrated in FIG. 8, The first pair of projections 172a and the second pair of projections 172b may be positioned on an opposite sides of the body portion 153. The third projection 174a and/or the fourth projection 174b may be elongated members which extend away from the body portion 153 of the engagement member 152. As will be discussed in greater detail below, it can be appreciated that the third projection 174a, the fourth projection 174b or both the third projection 174a and the fourth projection 174b may be designed to space the body portion 153 of the engagement member 152 away from a vessel wall.

Additionally, in some examples, the second pair of projections 172a (including the third projection 174a and/or the fourth projection 174b) may be "spring loaded." For example, the third projection 174a and/or the fourth projection 174b may be able to bend and/or flex such that it aligns with the body portion 153 of the engagement member 152 while the engagement member 152 is positioned within a delivery system. Further, the third projection 174a and/or the fourth projection 174b may shift to the configuration shown in FIG. 8 after the engagement member 152 is deployed out of the delivery system.

Figure 9:
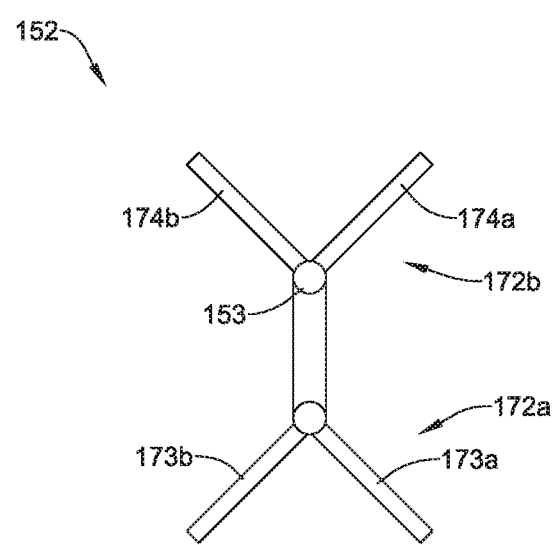
FIG. 9 illustrates a component of an example tissue retraction device.

FIG. 9 illustrates an end view of the engagement member 152 described in FIG. 8. For example, FIG. 9 shows the engagement member 152 including the first pair of projections 172a (including the first projection 173a and the second projection 173b) and the second pair of projections 172b (including the third projection 174a and the fourth projection 174b), whereby the first pair of projections 172a and the second pair of projections 172b are positioned on an opposite sides of the body portion 153.

Further, FIG. 9 illustrates that first projection 173a and the second projection 173b may extend away from the body portion 153 such that they extend away from one another. Similarly, FIG. 9 illustrates that third projection 174a and the fourth projection 174b may extend away from the body portion 153 such that they are on the opposite side of the body portion 153 from the first projection 173a and the second projection 173b and also such that they extend away from one another. This configuration may be beneficial because it permits the engagement member 152 to be spaced away from a vessel wall regardless of the orientation of the engagement member 152 takes as it is deployed from a delivery device.

FIGS. 10-20 illustrate a series of steps to deploy and utilize a tissue retraction system. An example tissue retraction device 122 may be utilized to lift and reposition target tissue which has been dissected by a clinician. The tissue retraction device 122 may be similar in form and function to the tissue retraction device 22 described above. As will be made clear by the following illustrations, as the clinician cuts the target tissue, the tissue retraction device 122 may lift and reposition the tissue, thereby providing the clinician with an unobstructed view of the ongoing procedure.

Figure 10:
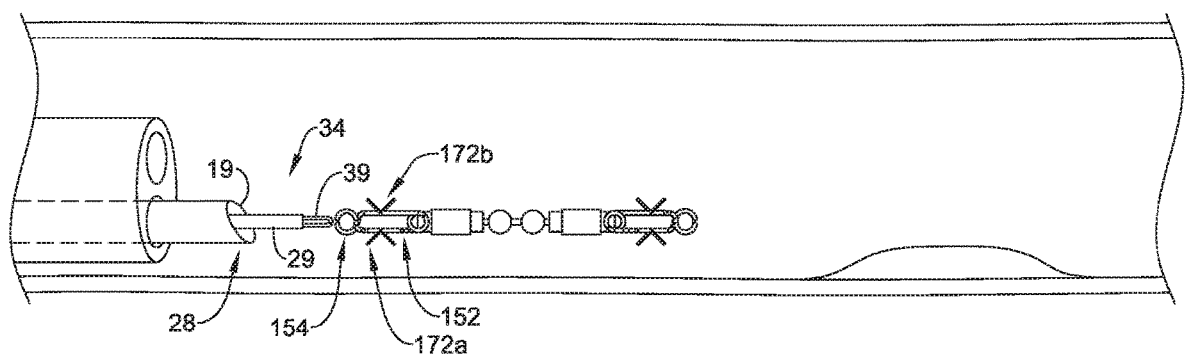
FIGS. 10-20 illustrate a methodology for deploying and attaching an example tissue retraction device.

FIG. 10 illustrates a first step in utilizing a tissue retraction system in a dissection procedure. As described above and illustrated in FIG. 10, the clinician may first advance the delivery catheter 26 and the delivery assembly 34 (including the actuation catheter 29 and the end effector 39) through the medical device 18 in a proximal-to-distal direction (relative to the distal end of the delivery catheter 26). This forward movement of the delivery assembly 34 (including the actuation catheter 29 and the end effector 39) may allow the end effector 39 to push the first end 154 of the tissue retraction device 122 in a distal direction and eventually out of the distal end of the delivery catheter 26. As discussed above, after having been advanced out of the lumen of the delivery catheter 26, FIG. 10 illustrates the first pair of projections 172a and the second pair of projections 172b of the engagement member 152 in a deployed configuration. FIG. 10 illustrates the tissue retraction device 122 having been advanced out of the distal end of the delivery catheter 26, whereby it is positioned adjacent to a tissue target site 50 (e.g., a cancerous lesion) located within a body lumen 16.

Figure 11:
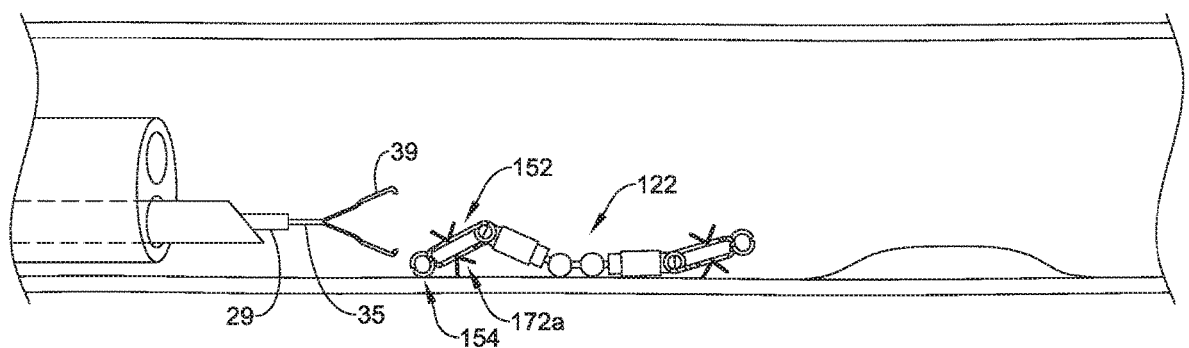

FIG. 11 illustrates an example second step in utilizing a tissue retraction system in a dissection procedure. FIG. 11 illustrates the actuation wire 35 being advanced in a proximal-to-distal direction, thereby positioning the tissue retraction device 122 adjacent to the inner surface of the body lumen 16. Further, FIG. 11 illustrates that the proximal-to-distal advancement of the actuation wire 35 through the lumen of the actuation catheter 29 permits the jaws of the end effector 39 to flex (e.g., shift) to an open configuration (as described above with respect to FIG. 5). Notwithstanding the methodology of opening the grasper described above, it is noted that a distal-to-proximal retraction of the actuation catheter 29 with respect to the actuation wire 35 may achieve the same result (e.g., opening the jaws of the end effector 39) as the proximal-to-distal advancement of the actuation wire 35 with respect to the actuation catheter 29. Additionally, in some examples an electromagnetic portion of the end effector 39 show in FIG. 11 may be activated after the end effector 39 has shifted to the open configuration.

Additionally, as compared to FIG. 10, FIG. 11 illustrates that the engagement member 152 is being spaced apart (e.g., held away) from the inner surface of the body lumen 16 by the first pair of projections 172a and the first end 154 of the engagement member 152. In other words, the engagement member 152 is contacting the inner surface of the body lumen 16 by three points of contact. As discussed, the three points of contact are the two projections of the pair of projections 172a and the first end 154 of the engagement member 152. Designing the engagement member 152 to be spaced from the inner surface of the body lumen 16 may be beneficial as it may reduce the possibility that a clinician will tear the body lumen 16 when attempting to capture the engagement member 152 within the end effector 39.

It is noted that, for simplicity purposes, the projections (e.g., the first pair of projections 172a, the second pair of projections 172b, etc.) are removed from FIGS. 12-20 (discussed below). However, it is contemplated that the projections may be included on any of the embodiments described herein.

Figure 12:
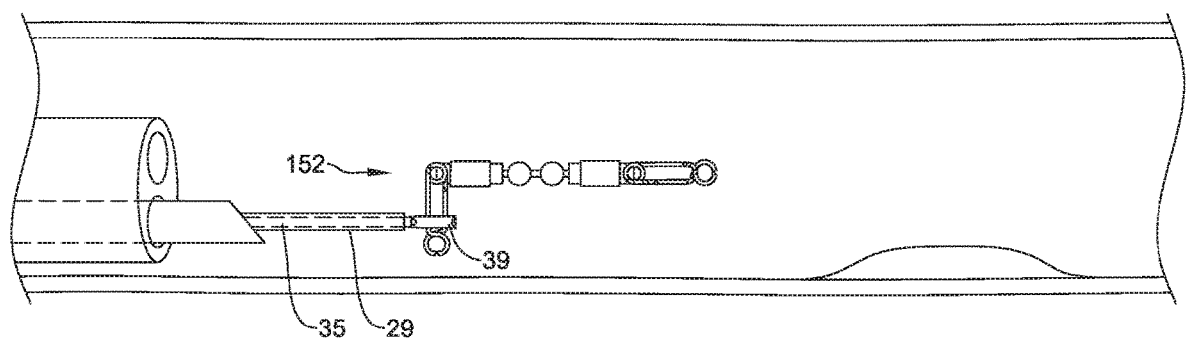

FIG. 12 illustrates an example third step in utilizing a tissue retraction system in a dissection procedure. FIG. 12 illustrates that the end effector (e.g., grasper) 39 has captured (e.g., acquired, grasped, received, etc.) the engagement member 152. The end effector's capture of the engagement member 152 may be achieved via the actuation of the end effector 39 as described above with respect to FIGS. 5-7. For example, it can be appreciated from FIG. 12 that the actuation wire 35 has been retracted in a distal-to-proximal direction within the lumen of the actuation catheter 29, thereby shifting the end effector 39 from an open position to a closed position (in which the legs of the end effector 39 squeeze closed around the engagement member 152). Additionally, in some examples, it can be appreciated that the engagement member 152 may include a ferromagnetic material. Accordingly, in some examples the engagement member 152 may have been drawn to the end effector 39 via activation of the electromagnetic portion of the end effector 39 (as described with respect to FIG. 11).

Figure 13:
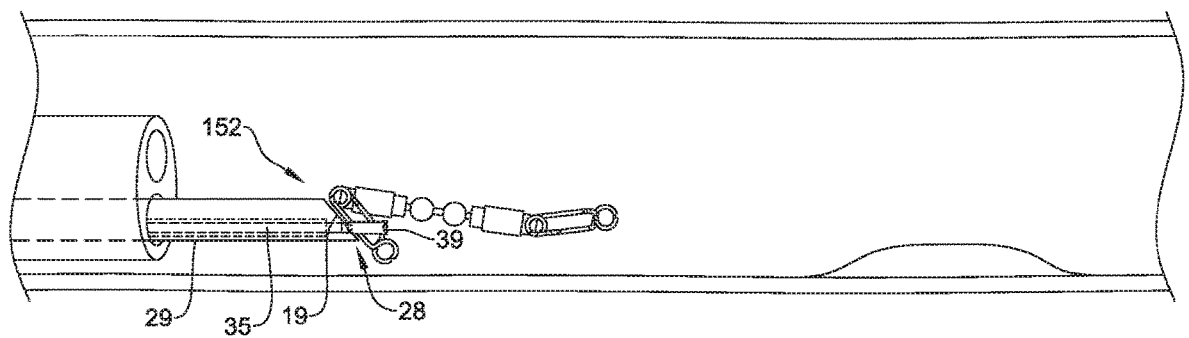

FIG. 13 illustrates an example fourth step in utilizing a tissue retraction system in a dissection procedure. FIG. 12 illustrates that the distal end of the delivery catheter 26 has been advanced in a proximal-to-distal direction out of the medical device 18 and toward the engagement member 152 (which has been captured by the end effector 39 as described above). FIG. 12 further illustrates that the distal end of the delivery catheter 26 has been advanced to a position in which the orienting tip 28 is positioned adjacent to the engagement member 152. Additionally, FIG. 12 illustrates that both the actuation wire 35 and the end effector 39 (the combination of which maintain the end effector in a closed configuration around the engagement member 152 as described above), have been retracted in a distal-to-proximal direction such that the engagement member 152 is drawn against the tapered face 19 of the engagement member orienting tip 28. It can be appreciated from FIG. 12, that the engagement member 152 is positioned at an angle defined by the tapered face 19 of the delivery catheter 26.

In some instances it may be beneficial for a clinician to change the orientation of the engagement member 152 after having captured it within the jaws of the end effector 39. For example, in some instances a clinician may need to pivot and/or rotate the engagement member 152 within the jaws of the end effector to position the engagement member 152 in a better orientation for attachment to a target site 50.

Figure 14:
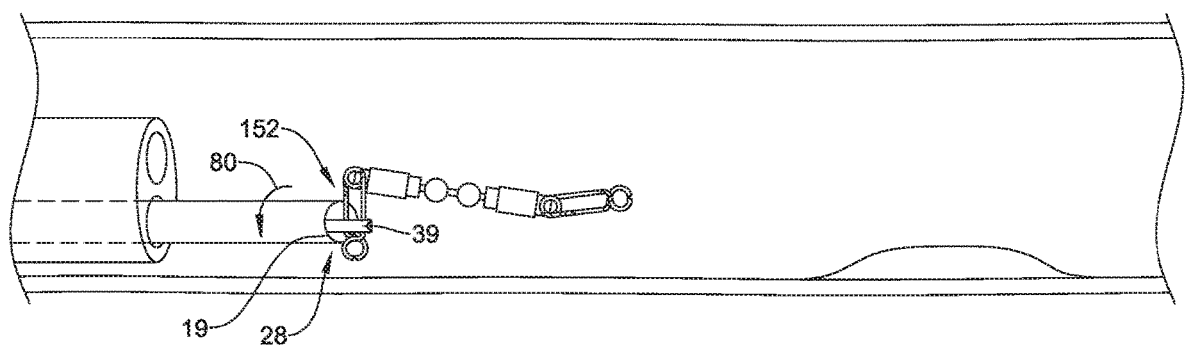
Figure 15:
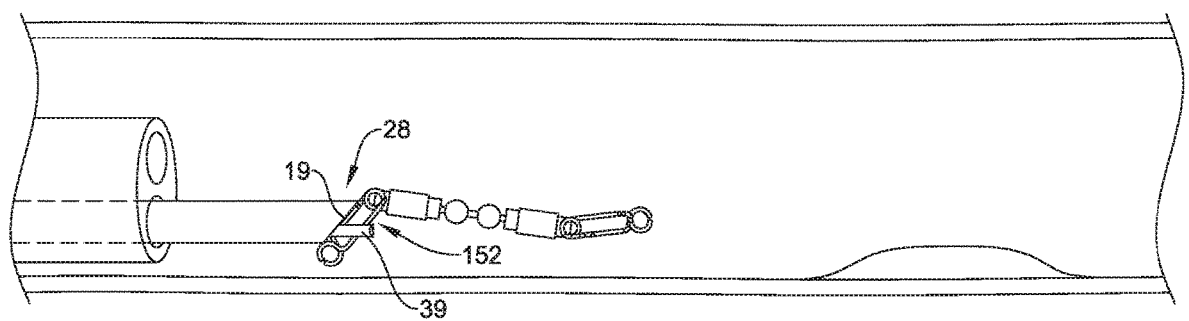

FIGS. 14-15 illustrates an example fifth step in utilizing a tissue retraction system in a dissection procedure. In particular, FIGS. 14-15 illustrate an example methodology for pivoting and/or rotating the orientation of the engagement member 152 while it remains within the jaws of the end effector. In particular, FIGS. 14-15 illustrate the rotation of the orienting tip 28 via rotation of the delivery catheter 26 via a proximal control member, as discussed above. For example, the arrow 80 illustrates the rotation of the orienting tip 28 (via rotation of the delivery catheter 26) while the end effector 39 remains drawn against the tapered face 19 of the orienting tip. The rotation of the orienting tip 28 may pivot (e.g., shift) the engagement member 152 within the opening (described above) of the engagement member. FIG. 14 illustrates that the engagement member 152 has been pivoted from the angled position shown in FIG. 13 to a position in which it is oriented substantially perpendicular to the longitudinal axis of the body lumen 16. FIG. 15 illustrates that the delivery catheter 26 has been further rotated (while the end effector 39 maintains the engagement member 152 drawn against the tapered face 19) such that the orienting tip 28 has pivoted the engagement member 152 to the angled orientation show in FIG. 15. It can be appreciated that the rotation of the orienting tip 28 may provide a clinician with the ability and control to position the engagement member 152 at any desired orientation with the body lumen 16.

Figure 16:
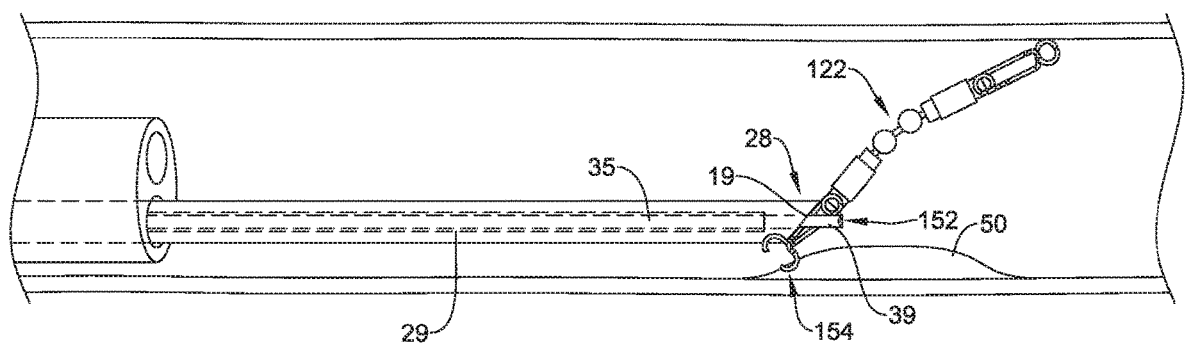

FIG. 16 illustrates an example sixth step in utilizing the tissue retraction system in a dissection procedure. FIG. 16 illustrates that a clinician may advance the orienting tip 28 of the delivery catheter along with the tissue retraction device 122 to a position in which the engagement member 152 (which is being held fixed against the orienting tip 28 by the combination of the actuation catheter 29 and the actuation wire 35) is adjacent the target tissue site 50 within the body lumen 16.

After the clinician has positioned the engagement member at the desired location adjacent the tissue target site 50, the clinician may manipulate the actuation catheter 29 in combination with the actuation wire 35 to attach the first end 154 of the engagement member 152 to the target tissue site 50. For example, the clinician may withdraw both the actuation catheter 29 and actuation wire 35 further into the lumen of the delivery catheter 26. It can be appreciated that withdrawing the actuation catheter 29 and actuation wire 35 further into the lumen of the delivery catheter 26 may pull the engagement member 152 against the tapered face 19 of the orienting tip 28. Further, pulling the engagement member 152 against the tapered face 19 of the orienting tip 28 may squeeze the arms of the engagement member 152 together, thereby opening the first end 154 of the engagement member 152. Once opened, the first end 154 of the engagement member 152 may be positioned onto the surface of the target tissue 50.

Figure 17:
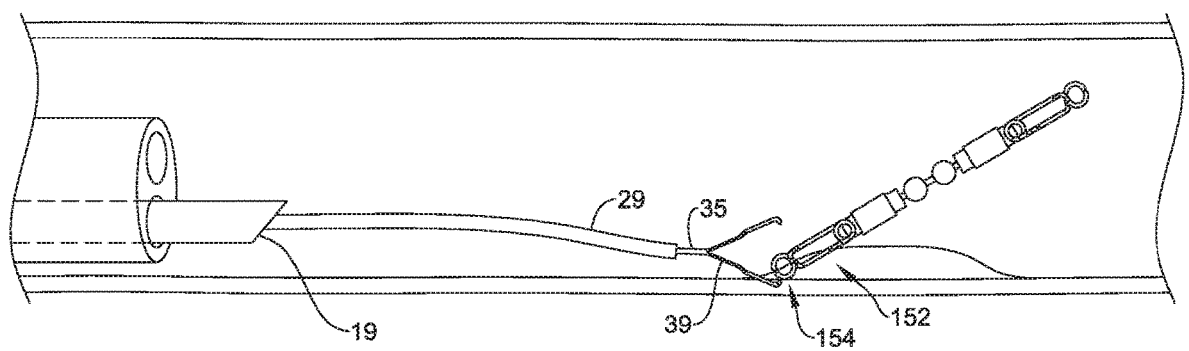

FIG. 17 illustrates an example seventh step in utilizing a tissue retraction system in a dissection procedure. After positioning the first end 154 of the engagement member 152 onto the surface of the target tissue 50, a clinician may withdraw both the delivery catheter 26 and the actuation catheter 29 in a distal-to-proximal direction. As described above, proximal retraction of the actuation catheter 29 relative to the actuation wire 35 may open the end effector 39, thereby allowing the first end 154 of the engagement member 152 to close and attach to the target tissue 50. In other words, proximal retraction of the actuation catheter 29 relative to the actuation wire 35 may shift the engagement member from an open configuration to a closed configuration.

Figure 18:
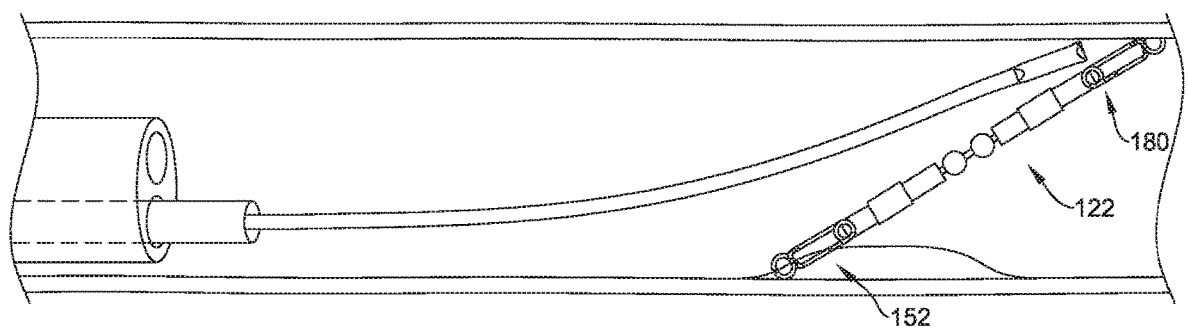

FIG. 18 illustrates an example eighth step in utilizing a tissue retraction system in a dissection procedure. In particular, FIG. 18 illustrates another engagement member 180 of the tissue retraction device 122 attached to the inner surface of the body lumen 16 (while the engagement member 152 remains attached to the target tissue 50). For simplicity purposes, it can be appreciated that the attachment of engagement member 180 of the tissue retraction device 122 to the inner surface of the body lumen 16 may be performed via the same series of steps described above to attach the engagement member 152 to the target tissue 50.

Figure 19:
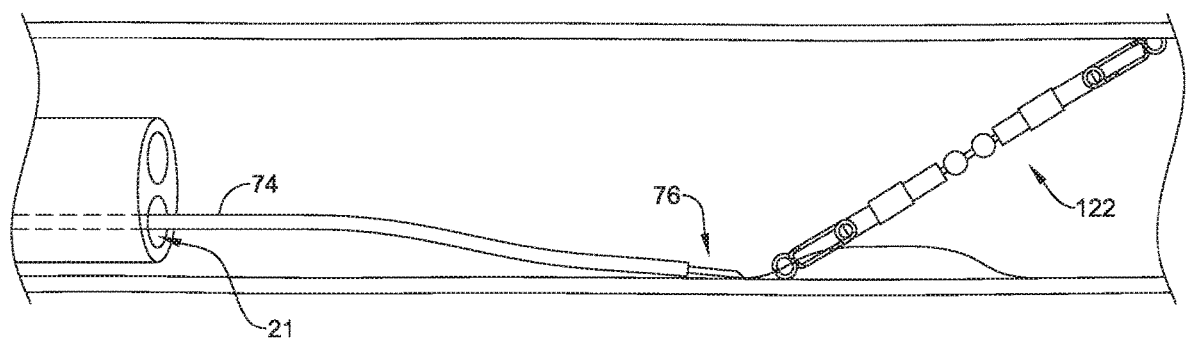

FIG. 19 illustrates an example ninth step in utilizing a tissue retraction system in a dissection procedure. FIG. 19 illustrates that after the tissue retraction device 122 has been attached to both the target tissue site 50 and to the inner surface of the body lumen 16 at a position spaced away from the target tissue site (which places the tissue retraction device 122 in tension), the clinician may exchange the delivery catheter, the actuation catheter and the actuation wire (including the end effector) for a cutting tool 74. The cutting tool 74 may include a cutting member 76 positioned at the target tissue 50. Further, the cutting tool 74 may be advanced within the working channel 21 of the medical device 18 as described above.

Figure 20:
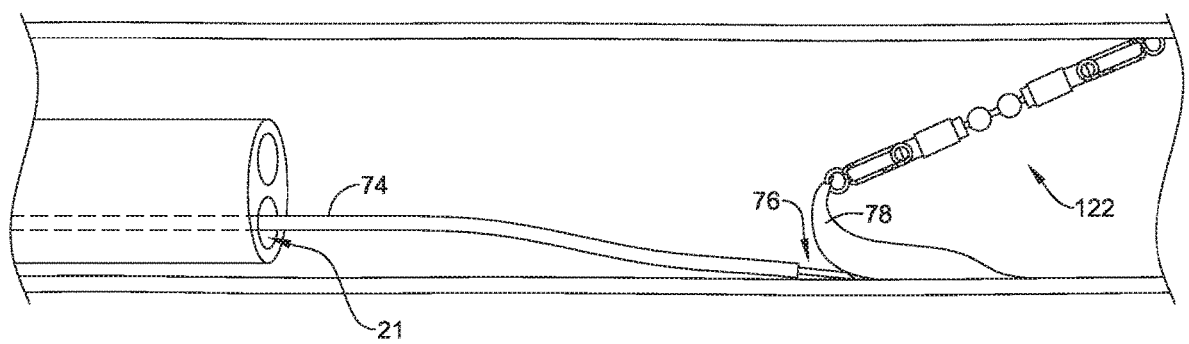

FIG. 20 illustrates an example tenth step in utilizing a tissue retraction system in a dissection procedure. FIG. 20 illustrates the clinician performing the tissue dissection by utilizing the cutting tool 74 to cut a portion of the target tissue 50. As can be appreciated from FIG. 20, as the cutting tool 74 cuts a portion of the target tissue 50, the tissue retraction device 122 retracts and lifts the dissected portion 78 of the target tissue 50 up and away from the plane of tissue being cut by the physician. By lifting and retracting the dissected portion 78 of the target tissue 50, a clear, unobstructed view of the procedure is maintained for the clinician. It is noted that, if necessary, the engagement members of the tissue retraction device 122 may be repositioned. In other words, adjustments in tension and/or direction may be imparted into the tissue retraction device 122 as desired.

It should be noted that the features of any of the tissue retraction systems described with respect to particular figures and/or embodiments are not limited to that particular example. Rather, it is contemplated that all of the features or examples disclosed with respect to a single example may be incorporated into any other example disclosed herein.

The materials that can be used for the various components of tissue retraction system 10 and the various devices disclosed herein may include those commonly associated with medical devices. For simplicity purposes, to the extent the following discussion makes reference to tissue retraction system 10, it is not intended to limit the devices and methods described herein only to tissue retraction system 10, as the discussion may be applied to other similar devices disclosed herein.

Tissue retraction system 10 and/or other components of tissue retraction system 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether)phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), styrene ethylene buthylene styrene (SEBS), Thermoplastic Elastomers (TPE) (such as Medalist® available from Teknor Apex and/or Mediprene® available from Hexpol TPE), polycarbonates, ionomers, biocompatible polymers, other suitable materials, or mixtures, combinations, copolymers thereof, polymer/metal composites, and the like. In some embodiments the sheath can be blended with a liquid crystal polymer (LCP).

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of tissue retraction system 10 and/or other components of tissue retraction system 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of tissue retraction system 10 and/or other components of tissue retraction system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of tissue retraction system 10 and/or other components of tissue retraction system 10 to achieve the same result.

In some embodiments, a degree of Magnetic Resonance Imaging (Mill) compatibility is imparted into tissue retraction system 10 and/or other components of tissue retraction system 10. For example, tissue retraction system 10 and/or other components of tissue retraction system 10, or portions thereof, may be made of a material that does not substantially distort the image and create substantial artifacts (e.g., gaps in the image). Certain ferromagnetic materials, for example, may not be suitable because they may create artifacts in an MRI image. Tissue retraction system 10 and/or other components of tissue retraction system 10, or portions thereof, may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A tissue retraction delivery device, comprising:
    a positioning assembly, the assembly including:
        a delivery catheter having a distal end region and a lumen extending therein, wherein the distal end region includes an engagement member orienting distal tip at an angle with respect to the longitudinal axis of the delivery catheter;
        an actuation catheter extending within at least a portion of the delivery catheter, the actuation catheter including a distal end region and a lumen extending therein;
        an actuation wire extending within the lumen of the actuation catheter, the actuation wire having a proximal end region and a distal end region; and
        an end effector coupled to the distal end region of the actuation wire, the end effector configured to capture an engagement member of a tissue retraction device;
    wherein manipulation of the actuation wire shifts the end effector from a first position to a second closed position.

2. The tissue retraction delivery device of claim 1, wherein the end effector includes a first leg having a first jaw and a second leg having a second jaw, and wherein the first jaw is configured to engage with the second jaw when in the closed position.

3. The tissue retraction delivery device of claim 2, wherein the first leg includes a first arcuate portion and the second leg includes a second arcuate portion, and wherein the first arcuate portion is designed to align with the second arcuate portion to define an opening therebetween when the end effector is in the closed position, and wherein the end effector is configured to receive the engagement member within the opening.

4. The tissue retraction delivery device of claim 1, wherein retracting the actuation wire within the lumen of the actuation catheter draws the engagement member into contact with the engagement member orienting distal tip of the delivery catheter.

5. The tissue retraction delivery device of claim 1, wherein contact of the engagement member with the distal end region of the delivery catheter actuates the engagement member from a first configuration to a second open configuration.

6. The tissue retraction delivery device of claim 1, wherein the distal tip of the delivery catheter includes a tapered face.

7. The tissue retraction delivery device of claim 6, wherein:
    retracting the actuation wire within the delivery-catheter draws the engagement member into contact with the tapered face of the distal tip of the delivery catheter; and
    rotation of the distal tip relative to the engagement member pivots the engagement member to change the orientation of the engagement member.

8. The tissue retraction delivery device of claim 1, wherein a portion of the end effector is magnetic.

9. The tissue retraction delivery device of claim 1, wherein the engagement member includes a projection member extending away from a body portion of the engagement member.

10. The tissue retraction delivery device of claim 1, wherein manipulation of the actuation wire with the engagement member extending transverse to the longitudinal axis of the delivery catheter draws the transversely oriented engagement member into contact with the angled distal tip of the delivery catheter to change the orientation of the engagement member.

11. The tissue retraction delivery device of claim 10, wherein rotation of the distal tip of the delivery catheter relative to the transversely oriented engagement member while the engagement member is drawn against the angled distal tip changes the orientation of the engagement member.

12. A tissue retraction delivery device, comprising:
    a handle;
    a delivery catheter having a proximal end coupled to the handle, a distal end region and a lumen extending therein, wherein the distal end region includes an engagement member distal tip at an angle with respect to the longitudinal axis of the delivery catheter; and
    an actuation assembly extending within the lumen of the delivery catheter, the actuation assembly including:
        an actuation catheter having a proximal end region and a distal end region;
        an actuation wire having a proximal end region and a distal end region; and
        a grasper coupled to the distal end region of the actuation wire, the grasper configured to receive an engagement member of a tissue retraction device;

wherein a portion of the actuation assembly is coupled to the handle; and wherein actuation of the handle shifts the grasper from a first position to a second closed position.

13. The tissue retraction delivery device of claim 12, wherein the grasper includes a first leg having a first jaw and a second leg having a second jaw, and wherein the first jaw is configured to mate with the second jaw when in the closed position.

14. The tissue retraction delivery device of claim 13, wherein:
the first leg includes a first arcuate portion and the second leg includes a second arcuate portion;
the first arcuate portion is designed to align with the second arcuate portion to define an opening therebetween when the grasper is in the closed position; and
the grasper is configured to receive the engagement member within the opening.

15. The tissue retraction delivery device of claim 12, wherein retracting the actuation wire within the actuation catheter draws the engagement member into contact with the engagement member distal tip of the delivery catheter.

16. The tissue retraction delivery device of claim 12, wherein contact of the engagement member with the distal end region of the delivery catheter actuates the engagement member from a first configuration to a second open configuration.

17. The tissue retraction delivery device of claim 12, wherein:
the distal tip includes a tapered face; and
retracting the actuation assembly within the delivery catheter draws the engagement member into contact with the tapered face of the distal tip of the delivery catheter.

18. The tissue retraction delivery device of claim 17, wherein rotation of the distal tip of the delivery catheter relative to the engagement member pivots the engagement member to change the orientation of the engagement member.

19. The tissue retraction delivery device of claim 12, wherein manipulation of the actuation wire with the engagement member extending transverse to the longitudinal axis of the delivery catheter draws the transversely oriented engagement member into contact with the angled distal tip of the delivery catheter to change the orientation of the engagement member.

20. A method of dissecting tissue, the method comprising:
advancing a tissue retraction device to a target site, the tissue retraction device including a positioning assembly, the positioning assembly including:
a delivery catheter having a distal end region and a lumen extending therein, wherein the distal end region includes an engagement member orienting tip, wherein the orienting tip includes a tapered face;
an actuation catheter extending within at least a portion of the delivery catheter, the actuation catheter including a distal end region and a lumen extending therein;
an actuation wire extending within the lumen of the actuation catheter, the actuation wire having a proximal end region and a distal end region; and
an end effector coupled to the distal end region of the actuation wire;
capturing an engagement member of the tissue retraction device within the end effector;
drawing the engagement member into contact with the distal end region of the delivery catheter;
engaging the engagement member with the tapered face of the orienting tip;
rotating the delivery catheter with respect to the engagement member to pivot the engagement member from a first position to a second position; and
attaching the engagement member to the target site.

* * * * *